(12) United States Patent
Mallard et al.

(10) Patent No.: US 11,224,566 B2
(45) Date of Patent: *Jan. 18, 2022

(54) COMPOSITION COMPRISING A CROSSLINKED HYALURONIC ACID (HA) IN COMBINATION WITH A LOW-MOLECULAR HA AND/OR AN AGENT STIMULATING ENDOGENOUS HA SYNTHESIS

(71) Applicant: GALDERMA HOLDING SA, La Tour-de-Peilz (CH)

(72) Inventors: Claire Mallard, Mougins (FR); Yves Rival, Antibes (FR)

(73) Assignee: Galderma Holding SA, La Tour-de-Peilz (CH)

( * ) Notice: Subject to any disclaimer, the term of this patent is extended or adjusted under 35 U.S.C. 154(b) by 5 days.

This patent is subject to a terminal disclaimer.

(21) Appl. No.: 16/453,813

(22) Filed: Jun. 26, 2019

(65) Prior Publication Data

US 2019/0314263 A1 Oct. 17, 2019

Related U.S. Application Data

(63) Continuation of application No. PCT/EP2017/084761, filed on Dec. 28, 2017.

(30) Foreign Application Priority Data

Dec. 29, 2016 (EP) .................................. 16306847

(51) Int. Cl.
| | |
|---|---|
| *A61K 8/73* | (2006.01) |
| *A61K 8/14* | (2006.01) |
| *A61K 8/9789* | (2017.01) |
| *A61K 8/35* | (2006.01) |
| *A61Q 19/08* | (2006.01) |

(52) U.S. Cl.
CPC ................ *A61K 8/735* (2013.01); *A61K 8/14* (2013.01); *A61K 8/35* (2013.01); *A61K 8/9789* (2017.08); *A61Q 19/08* (2013.01)

(58) Field of Classification Search
None
See application file for complete search history.

(56) References Cited

U.S. PATENT DOCUMENTS

| | | | |
|---|---|---|---|
| 5,019,174 A | 5/1991 | Wallach | |
| 5,792,472 A | 8/1998 | Roux et al. | |
| 5,830,499 A | 11/1998 | Bouwstra | |
| 5,908,697 A * | 6/1999 | Roux ................... | A61K 9/1272 428/402.2 |
| 6,017,520 A | 1/2000 | Synodis et al. | |
| 2007/0172442 A1 | 7/2007 | Saurat et al. | |
| 2013/0274221 A1 | 10/2013 | Paufique | |
| 2014/0039061 A1 | 2/2014 | Wiebensjo et al. | |
| 2015/0174033 A1* | 6/2015 | Herrmann ............... | A61K 8/35 424/49 |
| 2015/0272851 A1 | 10/2015 | Bourdon et al. | |
| 2015/0306022 A1* | 10/2015 | Chevreau ................. | A61K 8/41 424/729 |
| 2017/0151538 A1* | 6/2017 | Balooch ................ | A45D 44/005 |

FOREIGN PATENT DOCUMENTS

| | | |
|---|---|---|
| EP | 0 531 978 A2 | 3/1993 |
| FR | 2771635 A1 | 6/1999 |
| FR | 2939317 A1 | 6/2010 |
| WO | WO-2004/058796 A1 | 7/2004 |
| WO | WO-2014044808 A2 * | 3/2014 ............. A61Q 19/08 |
| WO | WO-2014/206500 A1 | 12/2014 |

OTHER PUBLICATIONS

Agerup et al ("NASHATM—the MONOGRAPH" (Jan. 2008)—an article retrieved from the Internet https://studyres.com/download/7856908) (Year: 2008).*
Fritze et al., "Remote loading of doxorubicin into liposomes driven by a transmembrane phosphate gradient", Biochimica et Biophysica Acta 1758, 2006 pp. 1633-1640 (8 pages).
No-Nonsense Cosmethic, "Sodium Hyaluronate Crosspolymer-2", Nov. 2011 (4 pages).
Wang et al., "In Vivo Stimulation of De Novo Collagen Production Caused by Cross-linked Hyaluronic Acid Dermal Filler Injections in Photodamaged Human Skin", Archives of Dermatology, American Medical Association, vol. 43, No. 2, Feb. 1, 2007, pp. 155-163 (9 pages).
Essendoubi et al., "Human skin penetration of hyaluronic acid of different molecular weights as probed by Raman spectroscopy", Skin Research and Technology, 2015 pp. 1-8 (8 pages).

* cited by examiner

*Primary Examiner* — Sin J Lee
(74) *Attorney, Agent, or Firm* — Foley & Lardner LLP; Sunit Talapatra (57) ABSTRACT

A composition comprising, in a physiologically acceptable medium, a crosslinked hyaluronic acid (HA), having a degree of modification less than 1.9 mole %; a HA with a molecular weight of about 50 kDa or less; and/or an agent stimulating endogenous HA synthesis. Also disclosed is a cosmetic use of such composition in skin care and/or anti-ageing treatment.

21 Claims, 1 Drawing Sheet

| | | Control | Formulation according to the invention |
|---|---|---|---|
| Fig. 1a | Hematoxylin/Eosin/ Saffron staining |  | |
| Fig. 1b | Movat's Pentachrome staining |  | |
| Fig. 1c | Cell nuclei (propidium iodide)<br><br>Biotin-HA bindng protein (SA-Alexa Fluor 488) |  | |
| Fig. 1d | Cell nuclei (propidium iodide)<br><br>Anti-procollagen I Ab (2nd Ab Alexa Fluor 488) |  | |

COMPOSITION COMPRISING A CROSSLINKED HYALURONIC ACID (HA) IN COMBINATION WITH A LOW-MOLECULAR HA AND/OR AN AGENT STIMULATING ENDOGENOUS HA SYNTHESIS

CROSS-REFERENCE TO RELATED APPLICATIONS

This application is a continuation of International Patent Application No. PCT/EP2017/084761 filed Dec. 28, 2017, published Jul. 5, 2018, as WO 2018/122344 A1, which claims priority to European Patent Application No. 16306847.1 filed Dec. 29, 2016. The contents of these applications are herein incorporated by reference in their entirety.

FIELD OF THE INVENTION

The invention relates to a composition comprising a stabilized crosslinked hyaluronic acid (HA) in combination with a HA with a molecular weight of about 50 kDa or less and/or an agent stimulating endogenous HA synthesis, as well as the uses of the composition in skin care and anti-ageing treatment.

BACKGROUND OF THE INVENTION

Ageing process occurs in every tissue in the human body, including skin, which is the most obvious indicator of age.

There are two distinct types of ageing. Ageing caused by the genes we inherit and depending on the passage of time is called chronological or intrinsic ageing. The other type of ageing is known as extrinsic ageing and is caused by environmental factors such as sun exposure (UV radiations), chemicals, microorganisms, food or environmental pollutants that can accelerate the ageing process. Age is not the determining factor in the condition of mature skin. Environmental factors that influence ageing of the skin play a central role. Tone, elasticity and epidermal regeneration capacity do not decline until advanced age in areas not exposed to light, whereas they do so prematurely in areas exposed to light. Young people who are exposed to a great amount of UV rays appear prematurely aged.

Intrinsic ageing, also known as the natural ageing process, is a continuous process that normally begins in the mid-twenties. Within the skin, collagen production slows down and elastin has a bit less spring. Dead skin cells do not shed as quickly and turnover of new skin cells may decrease slightly. While these changes usually begin in the twenties, the signs of intrinsic ageing are typically not visible for decades. The signs of intrinsic ageing are fine wrinkles, thin and transparent skin, loss of underlying fat, loss of density and firmness, which causes sagging skin, dry skin, and more dark spots.

With ageing, the loss of extracellular matrix and its major component hyaluronic acid (HA), which stabilizes the intracellular structures by forming viscoelastic network in which collagen and elastin fibers are embedded, induces loss of the skin mechanical functions. HA provides a cushion effect to the skin structures including the epidermis. Solidity of the skin is provided by the extracellular matrix and the loss of HA and consequently of the viscoelastic buffering system would contribute to easy tearing resulting in skin disruptions and skin dehydration leading to visible wrinkles on stratum corneum.

Viable epidermis and dermis are the essence of the skin. Structural destruction and loss of dermal collagen fiber bundles lead to wrinkling and increased appearance of muscular attachments. Irregular melanization leads to the apparition of lentigines, dark spots and melasma.

Most premature ageing is caused by sun exposure. Unlike chronological ageing, which depends on the passage of time, photoageing is directly correlated to the quantity of UV rays received during the course of lifetime. The effects of photodamage are often evident many years before intrinsic ageing is apparent. Individuals who have outdoor lifestyles, live in sunny climates and are lightly pigmented will experience the greatest degree of photoageing. All this factors influence extrinsic skin ageing process and can be distinguished from chronological ageing.

Ageing leads to a progressive decline in many biological functions in skin, eventually hindering cell division and growth. The biological signs of ageing involve both the epidermis and dermis layers characterized by decrease of epidermal thickness (that correlates with the reduced keratinocyte proliferation), reduction and disorganization of major key components, such as HA, collagens and other elastic fibers (proteoglycans and glycosaminoglycans), simultaneous increase in matrix metalloproteinases (MMP) production and flattening of the dermal-epidermal junction (DEJ). Collagens I and III, are the most abundant proteins in the dermis. They polymerize to form extended mechanically stiff fibrils, which confer tensile strength to the tissue. In addition to the fibrillar collagens, collagen VII is localized to perpendicularly oriented anchoring fibrils, which play a key role in securing the dermis to the DEJ. Skin ageing is associated to structural and compositional remodeling of dermal extracellular matrix (ECM) and basement membrane proteins. Histologic changes in skin associated with ageing are a reduced epidermal thickness and a flattened DEJ.

With age, skin homeostasis is disrupted, metabolic activities are slowed, and endogenous production and accumulation of reactive oxygen species (ROS) leading to oxidative cellular stress and secretion of inflammatory mediators leading to more reactive and sensitive skin.

Many contributions have been published focusing on the role of HA during epidermal homeostasis, in fibroblast physiology and ageing, during tumorigenesis and tumor progression and reflecting the impact of HA in cosmetics or regenerative medicine.

More particularly, an important function of HA is to hold water in the intercellular matrix of the connective tissue. This water-binding capacity significantly contributes to the elasticity of the skin, serving as a water reservoir. With ageing and UV-B damage, the quantity and quality of HA in the skin decreases, which leads a loss of elasticity and the increase of wrinkles. HA is then a skin hydrating agent that can help restore water to dehydrated skin.

HA is naturally found in the human body.

In the epidermis, HA content is especially high in proliferating basal regions. Histological findings suggest that basal layer keratinocytes contain intracellular HA, whereas extracellular HA prevails in upper epidermal layers. Extracellular HA is thought to maintain diffusion and to open up spaces to facilitate cell migration.

The main source of HA in the dermis is fibroblasts with higher HA synthesis activity in the papillary dermis. The high flexibility of HA strands and their hydrophilicity enable these molecules to fill in any gaps within the extracellular matrix. The large hydrodynamic volume of HA is mainly explained by multiple hydrogen bonds between adjacent disaccharides but may also rely on the close interaction of HA with highly glycosylated proteoglycans. The resulting viscoelastic properties of HA in the dermis account for its support of tissue architecture and possibly function as a kind of 'hydraulic shock absorber' in the dermis.

Endogenous HA in skin exhibits a high cellular turnover rate and its amount is regulated and balanced by synthesis and degradation process. In dermis, HA has a half-life of less than one day and the turnover in epidermis is reported to be more rapid with a half time of two to three hours. Production of HA quantities as high as 12-60 pg/cell/24 h has been reported in dermal fibroblasts, whereas keratinocytes produce about 10-fold less. Moreover, cutaneous HA concentration varies at different anatomical sites, for example, forearm skin contains twice as much HA as back skin.

Synthesis of HA in the skin is accomplished by three HA synthases (HAS1, HAS2, HAS3) that incorporate uridine diphosphate (UDP) sugars into the non-reducing end of the growing sugar chains. They produce different sizes of polysaccharide chains. HAS2 is considered as the main HA synthase in fibroblasts while HAS2 and HAS3 show comparable degrees of activity in keratinocytes. HAS activity depends on post-translational modifications such as precise ubiquitination, phosphorylation or N-glycosylation. HA degradation is achieved either enzymatically by hyaluronidases (HYAL) or non-enzymatically by mechanisms such as free-radical-related depolymerization occurring in the presence of reactive oxygen species. HYAL1 and HYAL2 are considered to be the main active HYALs in tissues. In skin, HA catabolism/degradation is thought to differ in epidermis and dermis. Extracellular HA degradation is thought to be initiated through liberation from the ECM network by non-enzymatic mechanisms.

Human cells do not always produce HA efficiently lifelong. By age and following menopause, HA production declines in skin resulting in joint pain, mycofacial rigidity, loss of elasticity, ageing, dryness and development of wrinkles. Topically applied, HA can complement the deficiencies in endogenous HA and can contribute to reduce signs of skin ageing.

Furthermore, the residence time of HA in tissues is only slightly dependent on molecular weight (i.e. exogenous HA of 100 000 Da has a half-life time of 10 h; exogenous HA of 6 000 000 Da has a half-life time of 13 h. Endogenous and exogenous hyaluronic acid generally has a molecular weight ranging from 1 to 10 million Da. Then, the most common way of prolonging the residence time of HA in tissue is by crosslinking. Crosslinked HA products can be chemically modified up to 50%.

We already know many compositions comprising HA alone or in combination with one or more other active ingredients for skin care, notably as anti-ageing and anti-wrinkle treatment.

For example, HA$^5$™ (from SKIN MEDICA) cream or lotion is a mix of five types of HA that smoothes the skin, thereby decreasing the appearance of fine lines and wrinkles. It comprises a time release HA for sustained release of HA, a sodium hyaluronate for immediate hydration, an uncrosslinked or "not crosslinked" HA for smoothness and hydration, a nano HA to soothe the skin and a crosslinked HA to provide long-lasting hydration for up to 8 hours. It further comprises VITISENSCE™ Technology that harnesses potent antioxidants found in Vitis flower stem cells extract, peptide complex to support rejuvenation and hydration, polysaccharides from French Polynesia, and plankton extract for healthy skin, all working to support skin's ability to replenish its own HA for overall skin health.

HA$^5$™ delivers both immediate and long-term benefits, instantly smoothes the appearance of fine lines and wrinkles, immediate hydration and improves the appearance of skin texture and roughness.

However, the degree of modification reflecting deviation from natural HA, traditional crosslinking relates to extensive modification, with high degree of synthetic (chemical) crosslinks that exceeds 10% and often reaches even 50% (10-50 crosslinker molecules per 100 HA-disaccharides). In doing so, the material is changed from being natural with physiological routes of degradation, to unnatural with limited ways of being eliminated from the body. The highly praised biocompatibility of natural HA will thus be substantially reduced in the highly crosslinked material so that the residence time in tissues is in fact shortened rather than prolonged due to inflammatory counter reactions. Then, such a degree of modification minimizes the strength, duration and biocompatibility of the crosslinked HA notably formulated as a gel.

We also know other skin care compositions (from TEOXANE LABORATORIES) comprising RHA resilient hyaluronic Acid™ (gel consisting of HA long chains stabilized by natural and mobile interactions supported by a lower crosslinker rate (1.9-4.0%)) and NOVHYAL™ (N-Acetyl Glucosamine-6-Phosphate) which reactivates the synthesis of HA in skin, thereby replumping the skin, in combination with a Dermo-Reconstructing Complex of antioxidants, amino acids, minerals and vitamin B6 which helps to reactivate the natural mechanisms of deep skin regeneration.

However, such compositions mainly promote long-lasting effect of HA without an instantly effective action.

In view of the above, there is a need to develop stabilized composition comprising an improved combination of cosmetic active ingredients on the basis of HA, by increasing the strength, duration and biocompatibility of the crosslinked HA and improving both immediate and long-lasting hydration of the skin.

SUMMARY OF THE INVENTION

A first object of the solution proposed by the invention to remedy this problem is to provide a composition comprising, in a physiologically acceptable medium:
  a crosslinked hyaluronic acid (HA), wherein the degree of modification of said crosslinked HA is less than 1.9 mole %;
  a HA with a molecular weight of about 50 kDa or less, preferably between 5 and 50 kDa, and/or
  an agent stimulating endogenous HA synthesis.

A second object is a cosmetic use of a composition as disclosed herein in skin care and/or anti-ageing treatment.

These and other features, aspects and advantages of the invention will become better understood with reference to the following description and drawings.

BRIEF DESCRIPTION OF THE DRAWINGS

The invention will now be described in more details, by way of example only, with reference to the accompanying drawings in which.

DETAILED DESCRIPTION OF THE INVENTION

The composition according to the invention comprises, in a physiologically acceptable medium, a crosslinked HA, wherein the degree of modification of said crosslinked HA is less than 1.9 mole %; a HA with a molecular weight of about 50 kDa or less, and/or an agent stimulating endogenous HA synthesis.

Physiologically Acceptable Medium

The composition as disclosed herein can comprise a physiologically acceptable medium widely employed in the art of drug and cosmetics manufacturing.

For instance, the physiologically acceptable medium may include a number of optional excipients at levels necessary to achieve desirable compositional aesthetics, fragrance presentation, or skin feel and conditioning benefits to the skin.

The following is a non-limiting disclosure of typical optional ingredients to be used together with the claimed invention:

abrasive agent, absorbent agent, anticaking agent, antidandruff agent, antifoaming agent, antimicrobial agent, antioxidant agent, antistatic agent, astringent agent, binding agent, bleaching agent, buffering agent, bulking agent, chelating agent, cleansing agent, cosmetic colorant agent, denaturant agent, deodorant, emollient, emulsifying agent, emulsion agent, emulsion stabilizing agent, film-forming agent, flavouring agent, foam boosting agent, gel forming agent, hair conditioning agent, hair fixing agent, humectant, masking agent, moisturizing agent, nail conditioning agent, opacifying agent, oral care agent, perfuming agent, plasticizer, preservative, refatting agent, refreshing agent, skin conditioning agent, skin protecting agent, smoothing agent, solvent, surfactant, tonic agent, UV-absorber, UV-filter and viscosity controlling agent.

Hyaluronic Acid

Hyaluronic acid or hyaluronan (or Hyaluronate) is a natural carbohydrate linear polysaccharide found in almost all living organisms. Its chemical structure is consisting of alternating repeating disaccharide units composed of D-glucuronic acid and N-acetylglucosamine linked together through alternating beta-1,4 and beta-1,3 glycosidic bonds. The number of repetitions can reach up to 10,000 with approximately from $10^2$ to $10^4$ kDa molecular weight.

Generally, the term "hyaluronic acid" can also encompass all variants and combinations of variants of hyaluronic acid, hyaluronate or hyaluronan, of various chain lengths and charge states, as well as with various chemical modifications, including crosslinking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of $-CH_2OH$ groups to $-CHO$ and/or $-COOH$; periodate oxidation of vicinal hydroxyl groups, optionally followed by reduction, e.g. reduction of $-CHO$ to $-CH_2OH$ or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

HA is a highly hydrophilic macromolecule which plays a key role in the transport of water in skin maintaining the hydration and stabilizing the structure of epidermis and dermis. HA plays an important role in the structural characteristics of many tissues. Due to its unique coil structure in aqueous solutions, HA exhibits a highly effective moisturizing property since it can retain till 1000 times its weight in water what makes HA so important for maintaining tissue structure and volume. Its remarkable water holding property and its unique viscoelastic and physicochemical properties, coupled with its lack of immunogenicity or toxicity, has led to the development of numerous HA-based medical devices and cosmetic and dermocosmetic products including skin moisturizers, osteoarthritis treatment, ophthalmic surgery, adhesion prevention after abdominal surgery, and wound healing.

Hyaluronic acid can be obtained from various sources of animal and non-animal origin. Sources of non-animal origin include yeast and preferably bacteria.

Crosslinked HA

The composition according to the invention compulsory comprises a crosslinked HA, wherein the degree of modification of said crosslinked HA is less than 1.9 mole %.

Crosslinked HA are often characterized in terms of "degree of modification", "crosslinking ratio", and "degree of crosslinking" (Keene et al., Carbohydrate Polymers, 2013, 91, 410-418).

The degree of modification (MoD) of HA generally ranges between 0.1 and 15 mole %. The degree of modification (mole %) describes the amount of crosslinking agent(s) that is bound to HA, i.e. molar amount of bound crosslinking agent(s) relative to the total molar amount of repeating HA disaccharide units. The degree of modification reflects to what degree the HA has been chemically modified by the crosslinking agent. Traditional crosslinking relates to extensive modification, with high degree of synthetic (chemical) crosslinks up to 40% (40 crosslinker molecules per 100 HA-disaccharides). In a preferred embodiment, the degree of modification of crosslinked HA with a chemical crosslinking agent is less than 15 mole %, preferably less than 1.9%, more preferably between 0.1 and 1.9 mole %.

Reaction conditions for crosslinking and suitable analytical techniques for determining the degree of modification are all well known to the person skilled in the art, who easily can adjust these and other relevant factors and thereby provide suitable conditions to obtain such a degree of modification and verify the resulting product characteristics with respect to the degree of modification.

Preferably, the degree of modification of hyaluronic acid according to the invention is in the range between 0.1 and 1.9 mole %, preferably about 1.0 mole %.

This results in obtaining an improved stabilized crosslinked HA with minimal modification, low degree of synthetic crosslinks and high degree of natural crosslinks (entanglements) which confers an optimized long-term effect of HA.

Crosslinked HA may also be characterized by the crosslinker ratio or crosslinking ratio (CrR). The cross-linker ratio (CrR) describes the proportion of total bound cross-linking agent (HA-X-HA and HA-X) that has bound two (or more) disaccharides (only HA-X-HA). The cross-linker ratio (CrR) of HA generally ranges between 0.01 and 0.50. In a preferred embodiment, the CrR is less than 0.30, preferably between 0.10 and 0.20, more preferably 0.10 or 0.20.

Crosslinked HA may also be characterized by the degree of crosslinking (CrD) corresponding to the stoichiometric ratio between the cross-linking agent that are double-linked and HA disaccharide units. In a preferred embodiment, the CrD is between 0.2 and 0.8, preferably between 0.2 and 0.5, more preferably between 0.2 and 0.4, even more preferably 0.2.

Crosslinking of the HA according to the invention may be achieved by modification with a chemical crosslinking agent.

The chemical crosslinking agent may for example be selected from the group consisting of divinyl sulfone, multiepoxides and diepoxides. According to an embodiment, the HA is crosslinked by a bi- or polyfunctional crosslinking agent comprising two or more glycidyl ether functional groups. According to a preferred embodiment, the chemical crosslinking agent is selected from the group consisting of 1,4-butanediol diglycidyl ether (BDDE), 1,2-ethanediol diglycidyl ether (EDDE) and diepoxyoctane. According to a more preferred embodiment, the chemical crosslinking agent is 1,4-butanediol diglycidyl ether (BDDE).

The crosslinked HA according to the invention may be a gel, or a hydrogel. That is, it can be regarded as a water-insoluble, but substantially dilute crosslinked system of HA molecules when subjected to a liquid, typically an aqueous liquid.

The gel contains mostly liquid by weight and can e.g. contain 90-99.9% water, but it behaves like a solid due to a three-dimensional crosslinked HA network within the liquid. Due to its significant liquid content, the gel is structurally flexible and similar to natural tissue.

Such a crosslinked HA according to the invention confers high gel strength, long duration and high biocompatibility.

The crosslinked HA according to the invention is then biocompatible. This implies that no, or only very mild, immune response occurs in the treated individual. That is, no or only very mild undesirable local or systemic effects occur in the treated individual.

As mentioned, crosslinking of HA to form the crosslinked HA gel may for example be achieved by modification with a chemical crosslinking agent, for example BDDE (1,4-butandiol diglycidylether). The HA concentration and the extent of crosslinking affects the mechanical properties, e.g. the elastic modulus G', and stability properties of the gel.

A BDDE (1,4-butanediol diglycidylether) crosslinked HA gel may for example be prepared according to the method described in Examples 1 and 2 of published international patent application WO 97/04012.

In a preferred embodiment, the HA of the composition according to the invention is at least present in the form of a sodium hyaluronate crosspolymer-2 (also called NASHA™ (Non-Animal Stabilized Hyaluronic Acid)), which is a crosslinked HA gel crosslinked by a chemical crosslinking agent, which is preferably 1,4-butanediol diglycidyl ether (BDDE), wherein the concentration of said HA is in the range of 10 to 30 mg/ml, the degree of modification with said chemical crosslinking agent is less than 1.9 mole %, more preferably about 1.0 mole %.

In particular, such a breakthrough technology significantly protects HA against biodegradation.

In a preferred embodiment, the crosslinked HA is into and/or onto a micro- or nanoparticular vesicles, which could also be designated as a capsule/sphere.

Among the micro- or nanoparticular vesicles, it is possible to use all carrier systems enabling controlled release of the HA according to the invention, such as microcapsules, microspheres, macromolecular complexes, nanospheres, nanocapsules or latex.

As non-limiting examples of micro- or nanoparticular vesicles, it is possible to cite the multilamellar vesicles NOVASOMES™, the multilamellar vesicles called SPHERULITES™, microcapsules based on polyurethane, polyurea resin, polyamide resin, polyamide-polyurea resin, polycarbonate resin, polysulphonate resin and polysulphonamide resin.

In a particular embodiment, vesicles are modified forms of liposomes or a variation of niosomes prepared from the mixture of monoester of polyoxyethylene fatty acids, cholesterol and free fatty acids at 74/22/4 ratio. They are also defined as non-phospholipid paucilamellar vesicles.

Preferably, vesicles consist of two to seven bilayered shells that surround an unstructured space occupied by a large amorphous core of hydrophilic or hydrophobic materials. These molecules have a hydrophilic head group attached to a hydrophobic tail and include long-chain fatty alcohols and derivatives, long-chain acids, long-chain amino and glycerolipids.

NOVASOMES™ are a preferred example of such vesicles.

In another particular embodiment, the vesicles are micro- or nanoparticular multilamellar vesicles constituted of concentric membranes comprise at least one non-ionic surfactant of the sucrose ester type comprising at least one chain arising from a linear or branched, saturated or unsaturated, optionally mono- or polyhydroxylated C12 to C22 fatty acid.

Preferably, the vesicles are multilamellar microvesicles, with an internal structure of concentric spherical bilayers made of water and amphiphile(s), created by the controlled shearing of liquid-crystalline phases. Application WO 97/00623 notably discloses carriers suitable for such vesicles, containing non-ionic surfactants forming onion-structured microcapsules within which an active material is encapsulated. Application WO 97/00623 also discloses compositions suitable for use as cosmetics containing at least one active material encapsulated in said microcapsules. U.S. Pat. No. 5,792,472 discloses a process of preparation of SPHERULITES™ with controlled size.

SPHERULITES™ are a preferred example of such vesicles.

In a further particular embodiment, the vesicles are multilamellar vesicles that encapsulate active ingredients. Particularly, they can be composed of surfactant bi-layers and aqueous interfaces. More particularly, they have a concentric structure.

In a further particular embodiment, the vesicles can comprise between 3 to 3000 surfactant bi-layers, preferably between 10 to 1000 surfactant bi-layers. Particularly, the vesicles can be hydrodispersible or lipodispersible. More particularly, the vesicles can encapsulate both of lipophilic or hydrophilic compounds, such as active agents.

The aqueous phase is particularly adapted for hydrophilic compounds whereas the surfactant bi-layer is particularly adapted for lipophilic actives.

In a preferred embodiment, the encapsulation rate of lipophilic or hydrophilic compounds is less than 20%. In a further preferred embodiment, the encapsulation rate of hydrophilic compounds is of 40% or less.

In a further particular embodiment, the vesicles as disclosed herein further comprise sucrose palmitate or sucrose tristearate with at least:

Tocopherol, tocopheryl acetate or butylene glycol;
Glyceryl linoleate or sodium benzoate;
Benzyl alcohol or phenoxyethanol; and eventually
Potassium sorbate, prunus Amygdalus Dulcis Oil or Citric Acid.

More preferably, the vesicles as disclosed herein comprise at least:

Sucrose palmitate;
Tocopheryl acetate;
Glyceryl linoleate; and
Phenoxyethanol.

Even more preferably, the vesicles as disclosed herein comprise:

Water;
Sucrose palmitate;
Tocopheryl acetate;
Glyceryl linoleate;
Phenoxyethanol;
Potassium sorbate; and
Citric acid.

In a further particular embodiment, the vesicles as disclosed herein can be either charged or non-charged. When these vesicles are charged, they are advantageously cationic. For example, the vesicles can be positively charged by addition of a cationic polymer such as guar hydroxypropyltrimonium chloride or a chitosan derivative such as chitosanide.

In a specific embodiment, the vesicles as disclosed herein are combined with an encapsulated material loaded into or onto said vesicles. Preferably, the encapsulated material is cross-linked acid (HA).

When vesicles are positively charged, the vesicles bind to skin and hair. They ensure a regular and controlled release of the encapsulated material at the surface of the skin and on the hair. Thus, even after a mechanical action, for example cleaning, the benefits of the composition according to the invention are preserved. This progressive release effect makes it possible to maintain the action of encapsulated material, such as HA, over time. The cationic vesicles optimize the activity on the skin surface by fixing themselves on the upper layers of the skin.

When the vesicles are not charged, they are called non-ionic. In this case, in addition to the aforementioned prolonged release effect, their presence promotes the diffusion of encapsulated material (HA) through the skin. Thus, the non-ionic vesicles bring the compounds into the deep layers of the skin by diffusing through epidermal layers and into the dermis.

In a particular embodiment, the compositions as disclosed herein comprise both cationic micro- or nanoparticular vesicles and non-ionic micro- or nanoparticular vesicles. In this case, the benefit lies in the respective contribution of each type of vesicles.

In a further particular embodiment, the micro- or nanoparticular vesicles have a diameter between 0.01 μm and 150 μm. If these vesicles are nanoparticular vesicles, their diameter is preferably between 0.1 μm and 0.5 μm and, if they are microparticle vesicles, their diameter is preferably between 1 μm and 50 μm.

Preferably, the micro- or nanoparticular vesicles diameter is between 0.1 μm and 20 μm, preferably between 0.1 μm and 5 μm, more preferably between 0.8 and 2 μm, more preferably 1 μm.

In particular, such vesicles significantly increase crosslinked HA absorption up to 90 μm into the skin layers.

The compounds that are encapsulated by the micro- or nanoparticular vesicles as disclosed herein are progressively released. The kinetics and thermodynamics of the release of the encapsulated compounds can be monitored. It has been shown that vesicles as disclosed herein can release compounds during 48 hours after application.

It has also been shown that the stability of the encapsulation technology is high. The vesicles show good tolerance to salt and a good stability from pH 3 to pH 9. The vesicles are thermosensitive and can be damaged at a temperature of more than 50° C.

In a further particular embodiment, vesicles can be incorporated at the end of the formulation at a temperature of less than 45° C. The vesicles can also be predispersed in water (50/50) under stirring if necessary. For low viscosity compositions such as for a shampoo for example, it is recommended to add a thickener in order to avoid sedimentation of the vesicles.

It has further been shown that, depending on the type of crosslinked HA used and/or depending on the concentration of said crosslinked HA, the composition as disclosed herein comprises crosslinked HA into or onto the micro- or nanoparticular vesicles. The crosslinked HA is loaded into and/or onto the micro- or nanoparticular vesicles. More preferably, the crosslinked HA is loaded onto the vesicles.

The term "into" encompasses the inside and the lower layers of the micro- or nanoparticular vesicles. The lower layers of the micro- or nanoparticular vesicles refers to the 30% of the layers that can be found between the center and the surface of the micro- or nanoparticular vesicles. More preferably, the term "into" refers only to the inside of the micro- or nanoparticular vesicles.

The term "onto" encompasses the surface and the upper layers of the micro- or nanoparticular vesicles. The upper layers of the micro- or nanoparticular vesicles refers to the 70% of the layers that can be found between the surface and the center of the micro- or nanoparticular vesicles. More preferably, the term "onto" refers only to the surface and to the 50% of the layers that can be found between the surface and the center of the micro- or nanoparticular vesicles.

The crosslinked HA according to the invention is preferably loaded into or onto the micro- or nanoparticular vesicles at a concentration of between 0.01% and 5% (w/w). More preferably the crosslinked HA is loaded into and/or onto the vesicles at a concentration of between 0.1% and 0.5% (w/w). Even more preferably, the crosslinked HA is loaded into or onto the micro- or nanoparticular vesicles at a concentration of 0.175%, 0.35% or 0.5% (w/w).

In a particular embodiment, the crosslinked HA is loaded into the micro- or nanoparticular vesicles as disclosed herein.

In another particular embodiment, the crosslinked HA is loaded onto the micro- or nanoparticular vesicles as disclosed herein.

It has been shown that, when the crosslinked HA is acid is sodium hyaluronate crosspolymer-2 (e.g. available under the trademark NASHA™), it is generally adsorbed onto the vesicles.

It has been shown that the advantages of using of sodium hyaluronate crosspolymer-2 loaded preferably on vesicles versus sodium hyaluronate crosspolymer-2 powder, is to have an improved skin penetration profile and to promote long lasting deeper hydration effect once applied onto the skin. Moreover, as compared to other encapsulated hyaluronic acids, the loading is twice higher. Finally, it has been shown that the use of sodium hyaluronate crosspolymer-2 as a crosslinked HA boosts hydration onto the skin by maintaining the skin barrier integrity.

The crosslinked HA loaded into and/or onto the vesicles as disclosed herein facilitates crosslinked HA absorption into the skin layers, protects crosslinked HA against biodegradation and increases time release of crosslinked HA.

Then, such a crosslinked HA loaded into and/or onto the vesicles improves skin hydration and moisturizing by increasing capacity to retain water providing instant smoothing effect and long lasting hydration into the epidermis. The skin seems more comfortable and flexible.

In a preferred embodiment, the crosslinked HA which is crosslinked by 1,4-butanediol diglycidyl ether (BDDE), with a degree of modification less than 1.9 mole %, more preferably about 1.0 mole % and loaded into and/or onto vesicles as disclosed herein at a concentration of 0.35% (w/w), has an improved skin penetration profile promoting long lasting deeper hydration effect once applied onto the skin.

Vesicles as crosslinked HA carrier foster the penetration of crosslinked HA according to the invention into the epidermis, increase their amount in the upper layers of the skin building a «reservoir effect» which will gradually release the crosslinked HA over time into the deeper layers of the skin.

Preferably, the composition as disclosed herein comprises from 0.1% to 10% by weight, for example from 0.5 to 5% by weight, for example from 1% to 3% by weight, and for example 1%, 2% or 3% by weight, of the crosslinked HA with a degree of modification of less than 1.9 mole %, preferably loaded into and/or onto the vesicles, relative to the total weight of the composition.

HA with a Low Molecular Weight ("Non Crosslinked HA")

In a particular embodiment, the composition comprises a crosslinked HA, wherein the degree of modification of said crosslinked HA is less than 1.9 mole %; and a HA (non crosslinked) with a molecular weight of about 50 kDa or less, preferably between 5 and 50 kDa, which is uniform, linear, un-branched and at least not crosslinked.

Preferably, the non crosslinked HA has a molecular weight between 20 and 50 kDa.

Although commonly used in commercial anti-wrinkle, anti-ageing, and moisturizing formulas, high molecular weight HA can actually not efficiently penetrate the barrier of the epidermis. Thus, these creams are not as effective as generally perceived. Further, once in the skin, the physiological effects of HA depend on the molecular size of the HA species present.

Very low molecular weight HA species, approximately 20 kDa or below, actually have pro-inflammatory effects and cause or increase inflammation. These HA species can bind to receptors on macrophages in the dermis, Toll-like receptor 2 and 4, and initiate an immune response. Although potentially useful for wound care, low molecular weight HA confers a negative effect in terms of skin aesthetics. In contrast, high molecular weight HA does not stimulate macrophages to initiate an inflammatory response. This indicates that selection of HA species to be used in cosmetic applications must be done carefully. The HA used must sufficiently penetrate the skin to elicit benefits but must do so without stimulating an immune response.

Then, low molecular weight HA of approximately 20-50 kDa according to the invention are ideal.

Indeed, this low molecular weight allows for increased permeation through the skin compared to high molecular weight HA. HA skin penetration depth depends on molecular weight and the lower is, the deeper penetration is.

In particular, such low molecular HA can maintain the epidermal cohesion and strengthens skin barrier integrity by increasing ZO-1, Occludin, Claudin-1 (tight junction proteins) and also Laminins expression which contribute to barrier formation, and increasing skin thickness and hydration. It also induces collagen 1 synthesis, a key structural dermis component by increasing pro-collagen 1 expression.

This low molecular HA can instantly rejuvenate the skin by improving its biomechanical and viscoelastic properties and significantly decreases deep wrinkles.

It can also significantly decrease skin roughness whereas higher have no measurable effect.

Preferably, the composition as disclosed herein comprises from 0.01% to 5% by weight, for example from 0.05 to 2% by weight, for example from 0.1% to 1% by weight, and for example 0.1%, 0.2%, 0.3%, 0.4% or 0.5% by weight, of the HA with a molecular weight of about 50 kDa or less, relative to the total weight of the composition.

Agent Stimulating Endogenous HA Synthesis

In another particular embodiment, the composition comprises a crosslinked HA, wherein the degree of modification of said crosslinked HA is less than 1.9 mole %; and an agent stimulating endogenous HA synthesis.

Indeed, an alternative way to improve a state resulting from a decrease in HA is to stimulate HA biosynthesis. Various materials promoting HA production have been proposed.

Preferably, the agent stimulating endogenous HA synthesis is selected from the group consisting of retinoids like retinoic acid, retinol, retinaldehyde and retinyl derivatives such as for example retinyl acetate, retinyl palmitate, retinyl retinoate, alpha-hydroxy acids such as lactic acid, citric acid, and glycolic acid, Transforming Growth Factor (TGF)-beta, several plant extracts and natural ingredients like yeast oligosaccharides from blue agave leaves (*Metschnikowia agaves*), *Articum lappa* fruit extract, isoflavone and saponin containing soy extract, *Ptychoverpa bohemica* extract, saffron extract, extract of seaweed belonging to the genus *Durvillea* of the family *Durvillea*, soybean isoflavone aglycones, 20-O-β-D-glucopyranosyl-20(S)-protopanaxadiol, soybean saponins such as soyasapogenol, and 6-paradol.

Indeed, retinoids like retinoic acid, retinol, retinaldehyde and retinyl derivatives such as for example retinyl acetate, retinyl palmitate, retinyl retinoate are known to increase epidermal HA biosynthesis in keratinocytes and are thus often used as anti-ageing ingredients in skin care products.

Alpha-hydroxy acids such as lactic acid, citric acid, and glycolic acid also stimulate HA biosynthesis in dermal fibroblasts.

Transforming growth factor (TGF)-beta is known to increase HA synthesis in dermal fibroblasts even if it appears to downregulate HA synthases in keratinocytes.

Furthermore, several plant extracts and natural ingredients were shown to upregulate HA biosynthesis in skin cells.

Thus, as a genuine booster of the endogenous synthesis of HA and expression of HAS2, PROHYAL+™ is an active ingredient rich in yeast oligosaccharides from blue agave leaves (*Metschnikowia agaves*).

Other examples relate to *Articum lappa* fruit extract which increases HAS-2 expression and HA level in human skin and an isoflavone and saponin containing soy extract also enhances the HA level in skin.

Other examples thereof include a *Ptychoverpa bohemica* extract, a saffron extract, and an extract of seaweed belonging to the genus *Durvillea* of the family *Durvillea*.

Soybean isoflavone aglycones also promote HA production. Furthermore, it is known that 20-O-β-D-glucopyranosyl-20(S)-protopanaxadiol (compound K), the main metabolite of ginseng saponin, increases expression of a HA synthase gene to promote HA production. Soybean saponins can be soybean saponin glycosides or soybean saponin aglycones. Particularly preferred examples of the soybean saponin aglycones include soyasapogenol A and/or soyasapogenol B. The soybean saponin glycoside can be extracted from cotyledon or germ of soybean or whole soybean by known methods. In addition to the soybean saponin, a material that is known to increase HA production, for example, one or more of plants such as yacon, crude drugs such as pueraria root, N-acetylglucosamine, peptides, and isoflavone aglycones could also be used.

A preferred agent stimulating endogenous HA is 6-paradol, having the following structure:

6-paradol (hydroxymethoxyphenyl decanone) is notably comprised in SYMDECANOX HA™ containing also caprylic/capric triglyceride, and reduces induction of reactive oxygen species with a free radicals scavenging activity and stabilization against oxidative degradation notably by increasing SOD-2 enzyme activity.

In addition, 6-paradol stimulates the dermal and epidermal HA level.

6-paradol mainly stimulates both dermal and epidermal HA synthesis. It also stimulates GAGs and extracellular matrix proteins like collagen I, collagen IV and elastins synthesis, inhibits MMPs and activates TIMPs (inhibitors of MMPs) synthesis, contributing to strengthen extracellular matrix and avoiding its degradation.

Furthermore, it inhibits the release of cytokines such as IL-6, IL-8, TNF-alpha and prostaglandins to reduce inflammation. In particular, inhibition of PGE-2 and TNF-alpha release prevents inflammatory reaction.

Preferably, the composition as disclosed herein comprises from 0.1% to 10% by weight, for example from 0.5 to 5% by weight, for example from 1% to 3% by weight, and for example 1%, 2% or 3% by weight, of the agent stimulating endogenous HA synthesis, relative to the total weight of the composition.

In another preferred embodiment, the composition as disclosed herein comprises i) a crosslinked HA, wherein the degree of modification of said crosslinked HA is less than 1.9 mole %, ii) a HA with a molecular weight of about 50 kDa or less, and iii) an agent stimulating endogenous HA synthesis; in a physiologically acceptable medium.

Anti-Ageing Active Ingredient

In another particular embodiment, the composition further comprises an anti-ageing active ingredient, preferably an anti-ageing plant extract.

The anti-ageing active ingredient enhances both immediate and long-lasting actions against ageing resulting from different variants of HA comprised in the composition or resulting from the agent stimulating endogenous HA synthesis. More particularly the anti-ageing active ingredient may complete or potentiate the activity of the agent stimulating endogenous HA synthesis.

The anti-ageing active ingredient is preferably an anti-ageing plant extract and more preferably an anti-ageing plant stem cells extract.

The plant stem cells extract is selected from the group consisting of *Malus domestica* Plant stem cells (PHYTOCELLTEC™), Glycerin (and) *Globularia cordifolia* Callus Culture Extract (RESISTEM™), edelweiss stem cells (*Leontopodium alpinum* stems cells having high concentration of leontopodic acids A and B) and *Plantago lanceolata* leaf extract (SENESTEM™), preferably *Plantago lanceolata* leaf extract.

*Malus domestica* are stem cells derived from the "Uttwiler Spätlauber", a rare Swiss apple variety. These apple stem cells are rich in epigenetic factors and metabolites which support the longevity of skin cells.

Glycerin (and) *Globularia cordifolia* Callus Culture Extract is a stem cell based anti-ageing body guard. Produced by plant cell culture, it offers various benefits pertaining to sustainability, safety, quality and sourcing. By mimicking defenses produced by hormesis, Glycerin (and) *Globularia cordifolia* Callus Culture Extract boost skin's ability to fight against pro-ageing agents and regenerate itself, protecting skin stem cells and stimulating sirtuin-1. In vivo, Glycerin (and) *Globularia cordifolia* Callus Culture Extract reduce micro-inflammations and redness, evening-out the complexion and enhancing skin's translucency and radiance.

*Leontopodium alpinum* stems G™ is rich of substances with antioxidant activity and inhibits collagenase thus limiting collagen degradation and skin firmness loss.

Preferably, the anti-ageing active ingredient is the *Plantago lanceolata* leaf extract which blocks the production of reactive oxidative species by reducing free radicals and increasing SOD-2 enzyme activity.

It inhibits ECM degradation by activating TIMPs (inhibitors of MMPs) and inhibiting MMPs synthesis. It increases Elastin and collagen I synthesis and strengthens the dermal-epidermal junction by producing Laminins and collagen IV.

It also increases the barrier cohesion by increasing ZO-1 and Claudin-1 expression and increases the epidermal thickness and participates to restoring epidermal homeostasis.

The *Plantago lanceolata* leaf extract further inhibits inflammatory cytokines (II-6, 11-8 TNF-alpha) and specific inflammatory mediators (PGE-2) to reduce inflammation.

Finally, it reduces specifically aged spots, notably on hands, by inhibiting the melanin synthesis in the melanocytes in the basal layer of epidermis contributing to reduce basal pigmentation and increase luminosity.

Preferably, the composition as disclosed herein comprises from 0.1% to 10% by weight, for example from 0.5 to 5% by weight, for example from 1% to 3% by weight, and for example 1%, 2% or 3% by weight, of the anti-ageing active ingredient, preferably anti-ageing plant extract, relative to the total weight of the composition.

In another preferred embodiment, the composition comprises:
- a crosslinked HA, wherein the degree of modification of said crosslinked HA is less than 1.9 mole %;
- a HA with a molecular weight of about 50 kDa or less;
- an agent stimulating endogenous HA synthesis; and
- an anti-ageing active ingredient.

Preferably, the composition comprises:
- a HA crosslinked with 1,4-butanediol diglycidyl ether (BDDE), having a degree of modification of about 1.0 mole % and being into and/or onto SPHERULITES™;
- a HA with a molecular weight of between 20 and 50 kDa;
- 6-paradol; and
- a *Plantago lanceolata* leaf extract.

Preferably, the composition comprises:
from 0.1% to 10% by weight, for example from 0.5 to 5% by weight, for example from 1% to 3% by weight, and for example 1%, 2% or 3% by weight, preferably 1% or 3%, of the HA crosslinked with 1,4-butanediol diglycidyl ether (BDDE), having a degree of modification of about 1.0 mole % and being loaded into and/or onto vesicles as disclosed herein relative to the total weight of the composition;

from 0.01% to 5% by weight, for example from 0.05 to 2% by weight, for example from 0.1% to 1% by weight, and for example 0.1%, 0.2%, 0.3%, 0.4% or 0.5% by weight, preferably 0.2%, of the HA with a molecular weight of between 20 and 50 kDa, relative to the total weight of the composition;

from 0.1% to 10% by weight, for example from 0.5 to 5% by weight, for example from 1% to 3% by weight, and for example 1%, 2% or 3% by weight, preferably 1%, of 6-paradol, relative to the total weight of the composition; and from 0.1% to 10% by weight, for example from 0.5 to 5% by weight, for example from 1% to 3% by weight, and for example 1%, 2% or 3% by weight, preferably 2%, of the *Plantago lanceolata* leaf extract, relative to the total weight of the composition.

Formulations

The compositions as disclosed herein are formulated for topical and/or parenteral application.

The compositions may be in any of the galenical forms normally employed for topical administration. Exemplary topical preparations include preparations in liquid, pasty or solid form, and more particularly in the form of ointments, aqueous, aqueous-alcoholic or oily solutions, dispersions of the optionally two-phase lotion type, serum, aqueous, anhydrous or lipophilic gels, powders, impregnated pads, syndets, wipes, sprays, foams, sticks, shampoos, compresses, washing bases, emulsions of liquid or semi-liquid consistency of the milk type, obtained by dispersion of a fatty phase in an aqueous phase (O/W) or vice versa (W/O), a microemulsion, suspensions or emulsions of soft, semi-liquid or solid consistency of the white or colored cream, gel or ointment type.

When they are for parenteral administration, the compositions according to the invention may be administered subcutaneously or intradermally. Exemplary parenteral compositions include compositions in the form of solutions or suspensions for perfusion or for injection.

Application

Another object of the invention is the cosmetic use of a composition according to the invention in skin care and/or anti-ageing treatment, notably for:
- decreasing and/or preventing the characteristics of wrinkles, small wrinkles and/or fine lines of the skin;
- improving and/or decreasing the microrelief of the skin;
- smoothing the skin;
- plumping the skin;
- improving the density of the skin;
- maintaining and/or restoring skin elasticity;—maintaining and/or restoring skin barrier integrity;
- maintaining and/or restoring skin firmness; and/or
- maintaining and/or restoring the cohesion of skin compartments, in particular the cohesion of the derm within the skin.

The composition as disclosed herein targets visible signs of skin ageing with complementary biological activities.

It mainly provides an improved instant and long lasting hydration with biological synergies of the active compounds. In particular, a sustained release of crosslinked HA may induce a deeper hydration.

It also promotes skin firmness, elasticity and density, with a smoothing effect on skin relief.

In particular, the composition according to the invention reduces fine lines and wrinkles with a soothing effect.

Furthermore, it increases luminosity and skin radiance, reduces aged spots, basal pigmentation and melanin content.

Indeed, aged skin is characterized by an increase in number and depth of wrinkles and increased skin dryness. The capacity of the skin to retain water decreases with age. Aged skin also exhibits decreased epidermal thickness, extracellular matrix degradation and flattening of the dermal-epidermal junction. With the age, skin becomes thinner, the barrier integrity is reduced and the skin is more sensitive and reactive. Inflammation and free radicals accelerate the age-related deterioration of the skin. Furthermore, following menopause, the dehydration is accelerated.

Further aspects and advantages of the invention will be disclosed in the following illustrative experimental section.

EXAMPLES

Example 1: In Vitro Studies

From in vitro studies, it results that the composition according to the invention prevents dermis degradation by increasing HA production, activating TIMPs and inhibiting MMPs, and also increasing Collagen I, Elastin, Collagen IV and Laminins synthesis.

The composition according to the invention also protects against inflammation by inhibiting the release of inflammatory cytokines (i.e. −91% IL-6 and −65% IL-8) and mediator of inflammation (i.e. −44% PGE2).

The composition according to the invention protects against free radicals (−77%) and increases SOD-2 enzyme activity (+33%).

The composition according to the invention restores skin barrier integrity by increasing ZO-1, Claudin-1 and Occludin expression.

Example 2: Ex Vivo Studies—Gene Expression/Extracellular Matrix Markers and Immunolabelling/Histology 2a. Compositions and Protocol:

The composition according to the invention which was tested comprised:
- *Plantago lanceolata* at 0.2% (0.2% ethanol)
- SPHERULITES 0.35% at 1% (10 mg/ml)
- caprylic/capric triglyceride and Hydroxymethoxyphenyl Decanone (SymDecanox HA) at 0.5% (1% ethanol)
- Hydrolyzed hyaluronic acid (PRIMALHYAL 50) at 0.5%

The placebo composition used as a comparative comprises ethanol 1.2%.

Explants from 3 donors were used:
1st donor: female, Black, 41 years, abdominoplasty;
2nd donor: female, Caucasian, 51 years, abdominoplasty; and
3rd donor: female, Caucasian, 45 years, abdominoplasty.

Upon receipt, skin explants were cut into pieces (4 cm$^2$), placed in culture medium and the association or the solvent control (ethanol at 1.2%) were topically applied (20 mg/cm$^2$) on the surface of the skin explants which were then incubated for 2 or 6 days (D2 or D6). A treatment renewal was performed after 48 hours of incubation for conditions with 6 days of incubation. In parallel, untreated skin explants (control condition) were also performed. All experimental conditions were performed in triplicate (n=3).

At the end of each incubation time, supernatants were discarded, skin explants were washed in a phosphate buffered saline solution (PBS) and 2 punches were performed on each explant (i.e. on each replicate):
- 1 punch of 4 mm diameter was immediately frozen at −80° C. for gene expression analysis
- 1 punch of 8 mm diameter was cut into two pieces with one half which was immediately frozen at −80° C. for immunolabeling experiments and the other half which was paraffin-embedded for histological staining.

The results are shown below.

2b. Gene Expression and Extracellular Matrix Markers:

The composition was applied topically 2 days and 6 days versus the placebo composition.

Gene expression was analyzed on donor 1 (by PCR Array mQPA-16 customized (2 values/condition)), on 16 targeted genes (2 house-keeping genes RPS28 and GAPDH; Keratinocyte differentiation markers=Calmodulin-like protein 5 (CALML5), Filaggrin (FLG), Keratin 10 (KRT10), Loricrin (LOR), Transglutaminase I (TGM1)), (Dermal epidermal junction markers=Collagen type IV alpha 1 (COL4A1), Collagen type 7 alpha 1 (COL7A1); Extra Cellular Matrix=Matrix metalloproteinase 3 (MMP3), Hyaluronan 3 (HAS3); Cytokines/Chemokines=Interleukin 8 (IL-8); Antimicrobial peptides/Innate immunity=Defensin beta 4A (DEFB4A), S100 calcium-binding protein A7/psoriasin (S100A7), Growth factors/Mitotic factors=Heparin-binding EGF-like growth factor (HBEGF); Oxidative and cellular stress response=Heat shock protein beta 1 (HSPB1)).

TABLE 1

Results on gene expression at Day 2

| | | | 2 days | |
| --- | --- | --- | --- | --- |
| | | | Composition according to the invention | |
| | Abbreviation | Control Cycles | Cycles | % Solvent control Mean HK |
| Housekeeping | RPS28 | 19.54 / 19.46 | 19.10 / 19.20 | 101 |
| | GAPDH | 20.07 / 20.14 | 19.82 / 19.76 | 99 |
| Keratinocyte differentiation | CALML5 | 22.31 / 22.44 | 21.70 / 21.95 | 116 |
| | FLG | 23.73 / 23.67 | 23.60 / 23.83 | 79 |
| | KRT10 | 18.08 / 17.98 | 17.04 / 17.13 | 152 |

TABLE 1-continued

Results on gene expression at Day 2

| | | | 2 days | |
| --- | --- | --- | --- | --- |
| | | | Composition according to the invention | |
| | Abbreviation | Control Cycles | Cycles | % Solvent control Mean HK |
| | LOR | 19.48 / 19.51 | 19.68 / 19.86 | 66 |
| | TGM1 | 24.70 / 24.64 | 24.11 / 24.10 | 117 |
| Dermal epidermal junction | COL4A1 | 28.48 / 28.24 | 28.70 / 28.73 | 62 |
| | COL7A1 | 26.67 / 26.61 | 25.68 / 25.73 | 151 |
| Extracellular matrix | MMP3 | 27.43 / 27.49 | 26.93 / 26.85 | 118 |
| | HAS3 | 30.91 / 31.18 | 29.57 / 29.74 | 207 |
| Cytokines/Chemokines | IL8 | 24.51 / 24.45 | 25.85 / 25.75 | 32 |
| Antimicrobial peptides, innate immunity | DEFB4A | 32.29 / 32.86 | 29.22 / 28.96 | 873 |
| | S100A7 | 24.90 / 24.86 | 23.65 / 23.52 | 195 |
| Growth factors/ Mitotic factors | HBEGF | 28.75 / 28.25 | 27.66 / 27.63 | 141 |
| Oxidative and cellular stress response | HSPB1 | 21.54 / 21.46 | 21.11 / 21.12 | 103 |

TABLE 2

Results on gene expression at Day 6

| | | | 6 days | |
| --- | --- | --- | --- | --- |
| | | | Composition according to the invention | |
| | Abbreviation | Control Cycles | Cycles | % Solvent control Mean HK |
| Housekeeping | RPS28 | 19.24 / 19.25 | 20.18 / 20.02 | 97 |
| | GAPDH | 19.99 / 20.01 | 20.69 / 20.79 | 105 |
| Keratinocyte differentiation | CALML5 | 21.77 / 21.67 | 21.79 / 21.95 | 158 |
| | FLG | 23.22 / 23.36 | 24.33 / 24.48 | 81 |
| | KRT10 | 17.11 / 17.20 | 19.98 / 20.04 | *24* |
| | LOR | 21.54 / 21.59 | 22.59 / 22.59 | 86 |
| | TGM1 | 23.72 / 23.80 | 22.33 / 22.36 | 467 |
| Dermal epidermal junction | COL4A1 | 29.30 / 28.95 | 31.94 / 31.75 | *26* |
| | COL7A1 | 26.55 / 26.50 | 27.99 / 28.08 | 62 |
| Extracellular matrix | MMP3 | 27.29 / 27.31 | 27.73 / 27.46 | 143 |
| | HAS3 | 31.69 / 31.80 | 28.43 / 28.53 | 1685 |
| Cytokines/Chemokines | IL8 | 25.29 / 25.36 | 24.71 / 24.32 | 310 |
| Antimicrobial peptides, innate immunity | DEFB4A | 32.82 / 33.18 | 30.66 / 30.89 | 816 |
| | S100A7 | 25.73 / 25.67 | 21.54 / 21.53 | 3143 |
| Growth factors/ Mitotic factors | HBEGF | 27.81 / 27.88 | 25.91 / 25.85 | 684 |

TABLE 2-continued

Results on gene expression at Day 6

|  |  | 6 days | |  |
|---|---|---|---|---|
|  |  | Composition according to the invention | | |
|  | Abbreviation | Control Cycles | Cycles | % Solvent control Mean HK |
| Oxidative and cellular stress response | HSPB1 | 20.46 20.24 | 21.17 21.14 | 100 | underlined: Up-regulated gene
in bold and italic: Down-regulated gene

The Tables show that HAS3, TGM1, S100A7, HBEGF, IL8 and DEFB4A genes are up-regulated after 2 days for HAS3/DEFB4A and after 6 days for HAS3/DEFB4/TGM1/IL8/S100A7/HBEGF with the composition. The composition according to the invention has thus a positive effect on gene expression related to actors involved in skin ageing.

Figure 1A:
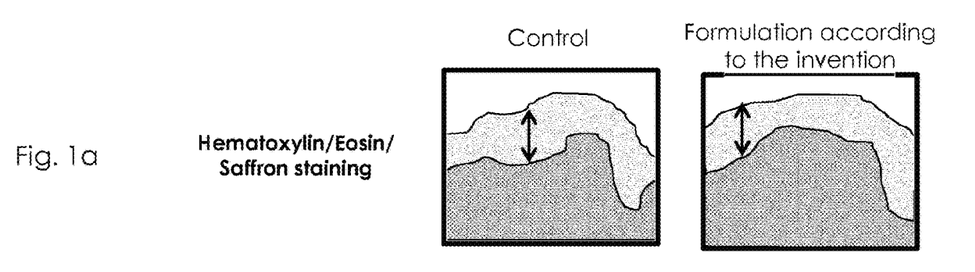
FIG. 1a is a schematic drawing of the effect of the composition according to the invention (described in Example 2a) on epidermis morphology shown by Hematoxylin/Eosin/Saffron staining.
Figure 1B:
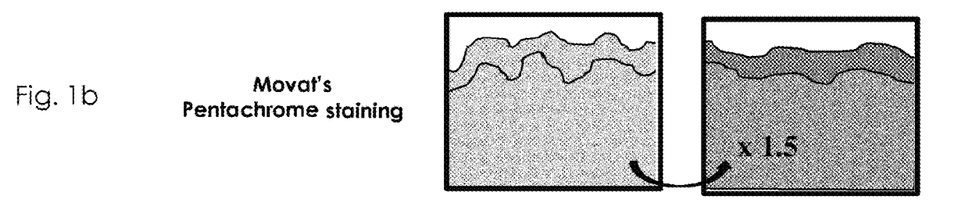
FIG. 1b is a schematic drawing of the effect of the composition according to the invention (described in Example 2a) on Elastin shown by Movat's Pentachrome staining.
Figure 1C:
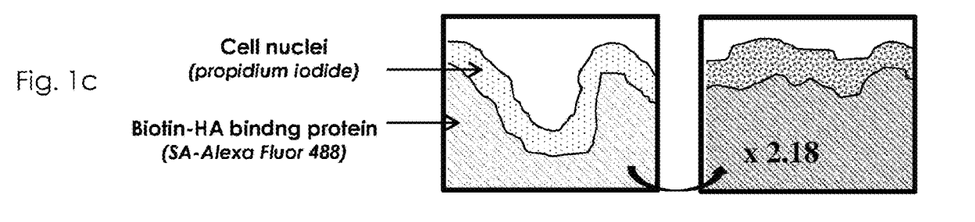
FIG. 1c is a schematic drawing of the effect of the composition according to the invention (described in Example 2a) on HA shown by Cell nuclei staining (propidium iodide) and Biotin-HA binding protein (SA-Alexa Fluor 488)
Figure 1D:
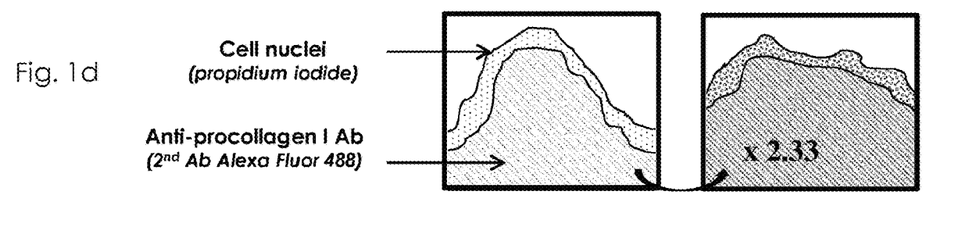
FIG. 1d is a schematic drawing of the effect of the composition according to the invention (described in Example 2a) on pro-collagen I shown by Cell nuclei staining (propidium iodide) and Anti-procollagen I Ab (2nd Ab Alexa Fluor 488).

FIGS. 1a to 1d particularly illustrate the results on skin explants markers from donor 1.
- The effect of the formulation according to the invention on epidermis morphology is shown by Hematoxylin/Eosin/Saffron staining (FIG. 1.a).
- The effect of the formulation according to the invention on Elastin is shown by Movat's Pentachrome staining (FIG. 1.b).
- The effect of the formulation according to the invention on HA is shown by Cell nuclei staining (propidium iodide) and Biotin-HA binding protein (SA-Alexa Fluor 488) (FIG. 1.c).
- The effect of the formulation according to the invention on pro-collagen I is shown by Cell nuclei staining (propidium iodide) and Anti-procollagen I Ab (2nd Ab Alexa Fluor 488) (FIG. 1.d).

Even if no significant effect on morphology with a similar epidermis thickness is observed after 6 days (FIG. 1.a), the composition according to the invention has a positive trend on elastin (×1,5) (FIG. 1.b) and a significant positive effect on HA (×2,18) (FIG. 1.c) and on pro-collagen 1 (×2,33) (FIG. 1.d).

2.c. Immunolabelling & Histology:

The composition according to the invention was topically applied during 2 Days and 6 days versus 1.2% Ethanol (placebo).

An immunohistochemistry analysis (IHC) was then performed (15 values/condition).

TABLE 3

| IHC results overview from the 3 donors | | | | | | | | | |
|---|---|---|---|---|---|---|---|---|---|
| Elastin % of vehicle | | Pro-collagen 1 % of vehicle | | Hyaluronic Acid % of vehicle | | Claudin 1 % of vehicle | | β-Defensin % of vehicle | |
| 2 days | 6 days | 2 days | 6 days | 2 days | 6 days | 2 days | 6 days | 2 days | 6 days |
| 1st Donor 111 | 150 | 154 | 233 | 89 | 218* | ND | ND | ND | ND |
| 2nd Donor 130 | 102 | 94 | 70 | 102 | 171 | 103 | 140 | 204 | 98 |
| 3rd Donor 134 | 115 | 128 | 98 | 127 | 169 | 191*** | 124 | 117 | 127 |

Unpaired Student's t-test (values 218* and 191*** are statistically different)

Even if we could observe variations between the three donors, the composition according to the invention led to an increase of HA at D6 for the three donors (with a significant increase for donor 1 at D6). For the two new donors tested, one could observe a trend in increasing Claudin-1 expression for donor 2 at D6 and a significant increase of Claudin-1 expression for donor 3 at D2.

The composition according to the invention involves a significant increase on HA for donor 1 at D6 and a tendency to increase for donor 2 and donor 3 at D6; a significant increase on Claudin-1 for donor 3 at D2 and a tendency to increase for donor 2 at D6; a tendency to increase on Elastin for donor 2 and donor 3 at D2 and a tendency to increase for donor 1 at D6; a tendency to increase on β-Defensin for donor 2 at D2 and no effect for donor 3; and a tendency to increase on pro-collagen I for donor 1 at D2 and D6

Example 3: Night Cream According to the Invention

| Ingredients | Range amount (% w/w) |
|---|---|
| Purified water | 45-60% |
| Emulsifiers | 2-5% |
| Thickening agent | 0.5-2% |
| Emollients | 4-6% |
| Humectants/Hydratants | 4-6% |
| NASHA SPHERULITES ™ | 1-3% |
| 6-paradol (Hydroxymethoxyphenyl decanone) and caprylic/capric triglycerides | 0.5-1.5% |
| Hyaluronic acid low molecular weight | 0.1-0.5% |
| Glycerin, Plantago lanceolata leaf extract (and) xanthan gum | 1.5-2.5% |
| Retinol | 0.01-0.5% |
| Skin protectant actives | 15-20% |
| Preservatives | 0.5-1% |

Example 4: Anti-Ageing Serum According to the Invention

| Ingredients | Range amount (% w/w) |
|---|---|
| Purified water | 55-70% |
| Emulsifiers | 0.5-1% |
| Thickening agent | 0.5-1.5% |
| Emollients | 7-11% |
| Humectants/Hydratants | 2-5% |
| NASHA SPHERULITES ™ | 1-3% |
| 6-paradol (Hydroxymethoxyphenyl | 0.5-1.5% |

| Ingredients | Range amount (% w/w) |
| --- | --- |
| decanone) and caprylic/capric triglycerides | |
| Hyaluronic acid low molecular weight | 0.1-0.5% |
| Glycerin, Plantago lanceolata leaf extract (and) xanthan gum | 1.5-2.5% |
| Skin antiageing actives | 4-8% |
| Skin protectant actives | 7-12% |
| Preservatives | 0.5-1% |

Example 5: Brightening Serum According to the Invention

| Ingredients | Range amount (% w/w) |
| --- | --- |
| Purified water | 40-60% |
| Emulsifiers | 3-5% |
| Thickening agent | 0.4-1% |
| Emollients | 8-15% |
| Humectants/Hydratants | 1-4% |
| NASHA SPHERULITES ™ | 1-3% |
| 6-paradol (Hydroxymethoxyphenyl decanone) and caprylic/capric triglycerides | 0.5-1.5% |
| Hyaluronic acid low molecular weight | 0.1-0.5% |
| Glycerin, Plantago lanceolata leaf extract (and) xanthan gum | 1.5-2.5% |
| Retinol | 0.01-0.5% |
| Skin brightening actives | 3-5% |
| Skin protectant actives | 15-20% |
| Preservatives | 0.5-1% |

Example 6: Daily Moisturizer SPF30 Untinted According to the Invention

| Ingredients | Range amount (% w/w) |
| --- | --- |
| Purified water | 45-55% |
| Emulsifiers | 3-5% |
| Thickening agent | 0.5-3% |
| Emollients | 8-15% |
| Mineral sunscreens | 8-12% |
| Organic sunscreens | 9-13% |
| NASHA SPHERULITES ™ | 1-3% |
| Hyaluronic acid low molecular weight | 0.1-0.5% |
| Humectants/Hydratants | 1-5% |
| Skin protectant actives | 4-7% |
| Preservatives | 0.5-1% |

Example 7: Daily Moisturizer SPF30 Tinted According to the Invention

| Ingredients | Range amount (% w/w) |
| --- | --- |
| Purified water | 45-55% |
| Emulsifiers | 3-5% |
| Thickening agent | 0.5-3% |
| Emollients | 8-15% |
| Mineral sunscreens | 8-12% |
| Organic sunscreens | 9-13% |
| NASHA SPHERULITES ™ | 1-3% |
| Hyaluronic acid low molecular weight | 0.1-0.5% |
| Humectants/Hydratants | 1-5% |

| Ingredients | Range amount (% w/w) |
| --- | --- |
| Skin protectant actives | 4-7% |
| Cosmetic pigments | 0.3-0.4% |
| Preservatives | 0.5-1% |

Example 9: Eye Serum According to the Invention

| Ingredients | Range amount (% w/w) |
| --- | --- |
| Purified water | 55-75% |
| Emulsifiers | 1-3% |
| Thickening agent | 0.5-1.5% |
| Emollients | 5-7% |
| Humectants/Hydratants | 3-7% |
| NASHA SPHERULITES ™ | 1-3% |
| 6-paradol (Hydroxymethoxyphenyl decanone) and caprylic/capric triglycerides | 0.5-1.5% |
| Hyaluronic acid low molecular weight | 0.1-0.5% |
| Glycerin, Plantago lanceolata leaf extract (and) xanthan gum | 1.5-2.5% |
| Skin protectant actives | 17-23% |
| Preservatives | 0.5-1% |

The invention claimed is:

1. A composition comprising, in a physiologically acceptable medium:
    (a) a crosslinked hyaluronic acid, wherein the degree of modification of the crosslinked hyaluronic acid is less than 1.9 mole %, and wherein the crosslinked hyaluronic acid is loaded onto and/or into a first population of non-ionic vesicles and a second population of cationic vesicles, wherein both the first and second populations of vesicles comprise micro- and/or nanoparticular vesicles; and
    (b) a non-crosslinked hyaluronic acid with a molecular weight of 50 kDa or less and an agent stimulating endogenous hyaluronic acid synthesis.

2. The composition of claim 1, further comprising an anti-aging active ingredient.

3. The composition of claim 2, wherein the anti-aging active ingredient is an anti-aging plant extract.

4. The composition of claim 3, wherein the anti-aging plant extract is selected from the group consisting of *Malus domestica* plant stem cells, glycerin and *Globularia cordifolia* callus culture extract, edelweiss plant stem cells, and *Plantago lanceolata* leaf extract.

5. The composition of claim 2, wherein the anti-aging active ingredient is *Plantago lanceolata* leaf extract.

6. The composition of claim 1, wherein the degree of modification of the crosslinked hyaluronic acid is between 0.1 and 1.9 mole %.

7. The composition of claim 1, wherein the degree of modification of the crosslinked hyaluronic acid is 1.0 mole %.

8. The composition according to claim 1, wherein the crosslinked hyaluronic acid is sodium hyaluronate crosspolymer-2.

9. The composition of claim 1, wherein the non-crosslinked hyaluronic acid has a molecular weight between 20 kDa and 50 kDa.

10. The composition of claim 1, wherein the agent stimulating endogenous hyaluronic acid synthesis is selected from the group consisting of retinoids, retinyl derivatives, alpha-hydroxy acids, Transforming Growth Factor beta, plant extracts, and natural ingredients.

11. The composition according to claim 1, wherein the agent stimulating endogenous hyaluronic acid synthesis is 6-paradol.

12. The composition according to claim 1, wherein the crosslinked hyaluronic acid is loaded onto and/or into the first and second populations of vesicles at a concentration between 0.01% and 5% (w/w).

13. The composition according to claim 1, wherein the crosslinked hyaluronic acid is loaded onto and/or into the first and second populations of vesicles at a concentration of 0.175%, 0.35%, or 0.5% (w/w).

14. The composition according to claim 1, wherein the first population of non-ionic vesicles are multilamellar vesicles comprising concentric membranes comprising at least one non-ionic surfactant of the sucrose ester type comprising at least one chain arising from a linear or branched, saturated or unsaturated, optionally mono- or polyhydroxylated, C12 to C22 fatty acid.

15. The composition of claim 14, further comprising an anti-aging active agent comprising *Plantago lanceolate* leaf extract, and wherein:
    (a) the crosslinked hyaluronic acid is crosslinked with 1,4-butanediol diglycidyl ether and has a degree of modification of 1.0 mole %;
    (b) the non-crosslinked hyaluronic acid has a molecular weight of between 20 kDa and 50 kDa; and
    (c) the agent stimulating endogenous hyaluronic acid synthesis is 6-paradol.

16. The composition of claim 15, comprising, relative to the total weight of the composition:
    (a) 0.1 to 10% by weight of the crosslinked hyaluronic acid, wherein the crosslinked hyaluronic acid is crosslinked with 1,4-butanediol diglycidyl ether and has a degree of modification of 1.0 mole %;
    (b) 0.01 to 5% by weight of the non-crosslinked hyaluronic acid;
    (c) 0.1 to 10% by weight of 6-paradol; and
    (d) 0.1 to 10% by weight of *Plantago lanceolata* leaf extract.

17. The composition according to claim 1, wherein the composition is formulated for topical or parenteral application.

18. A method of caring for skin or reducing the effects of skin ageing, the method comprising topically applying the composition according to claim 1 to the skin of a human subject in need thereof.

19. The composition according to claim 12, wherein
    (a) the first population of non-ionic vesicles comprise microparticular vesicles and the second population of cationic vesicles comprise microparticular vesicles;
    (b) the first population of non-ionic vesicles comprise nanoparticular vesicles and the second population of cationic vesicles comprise nanoparticular vesicles;
    (c) the first population of non-ionic vesicles comprise microparticular vesicles and the second population of cationic vesicles comprise nanoparticular vesicles; or
    (d) the first population of non-ionic vesicles comprise nanoparticular vesicles and the second population of cationic vesicles comprise microparticular vesicles.

20. The composition according to claim 1, wherein the first and second populations of vesicles comprise vesicles having a diameter of between 0.01 μm and 150 μm.

21. The composition according to claim 1, wherein the first and second populations of vesicles comprise:
    (a) microparticular vesicles having a diameter of between 1 μm and 50 μm, and/or
    (b) nanoparticular vesicles having a diameter of between 0.01 μm and 0.5 μm.

\* \* \* \* \*